United States Patent
Tsukioka (10) Patent No.: US 9,517,497 B2
(45) Date of Patent: Dec. 13, 2016

(54) RINSING DEVICE FOR MICROPLATE

(71) Applicant: MEDICATEC Inc., Yashio-shi, Saitama (JP)

(72) Inventor: Hiroyasu Tsukioka, Soka (JP)

(73) Assignee: MEDICATEC Inc., Yashio-shi (JP)

( * ) Notice: Subject to any disclaimer, the term of this patent is extended or adjusted under 35 U.S.C. 154(b) by 592 days.

(21) Appl. No.: 13/942,848

(22) Filed: Jul. 16, 2013

(65) Prior Publication Data

US 2014/0020724 A1    Jan. 23, 2014

(30) Foreign Application Priority Data

Jul. 20, 2012   (JP) ................................ 2012-161460

(51) Int. Cl.
- *B08B 9/08* (2006.01)
- *G01N 35/10* (2006.01)
- *B01L 99/00* (2010.01)

(52) U.S. Cl.
CPC .................. *B08B 9/08* (2013.01); *B01L 99/00* (2013.01); *G01N 35/1004* (2013.01); *B01L 2300/0829* (2013.01); *B01L 2400/0487* (2013.01); *B01L 2400/065* (2013.01)

(58) Field of Classification Search
CPC . B08B 9/0323; B08B 9/08; G01N 2035/1006; G01N 35/1004; B01L 2300/0829; B01L 2400/0478; B01L 2400/0487; B01L 2400/065; B01L 2200/026; B01L 99/00

See application file for complete search history.

(56) References Cited

U.S. PATENT DOCUMENTS

| 4,635,665 A | 1/1987 | Namba et al. |
| 2003/0213504 A1* | 11/2003 | Cerra .................... B08B 9/0323 134/23 |

FOREIGN PATENT DOCUMENTS

| EP | 0903181 A2 | 3/1999 |
| EP | 1046823 A2 | 10/2000 |
| JP | S48-82899 A | 11/1973 |
| JP | S59-119383 U | 8/1984 |
| JP | H7-83939 A | 3/1995 |
| JP | H7-113728 A | 5/1995 |

(Continued)

OTHER PUBLICATIONS

The Japanese office action letter issued on Nov. 24, 2015 in the counterpart Japanese patent application.

(Continued)

*Primary Examiner* — Michael Barr
*Assistant Examiner* — Irina Graf
(74) *Attorney, Agent, or Firm* — Mots Law, PLLC (57) ABSTRACT

A rinsing device is comprised of a rinsing head including a first flow path extending horizontally, and a second flow path extending horizontally and being disposed below or above the first flow path so as not to communicate with the first flow path; one or more nozzles arranged horizontally and projecting vertically downward from the rinsing head; and one or more sliding members including passages in fluid communication with the nozzles, the sliding members slidably fitting in the rinsing head and being movable between a first position to place the passages in fluid communication with the first flow path and a second position to place the passages in fluid communication with the second flow path.

3 Claims, 6 Drawing Sheets

(56) References Cited

FOREIGN PATENT DOCUMENTS

| JP | 2001-035862 A | 2/2001 |
|---|---|---|
| JP | 2002-243733 A | 8/2002 |
| JP | 2003-185660 A | 7/2003 |
| WO | 9714041 A1 | 4/1997 |

OTHER PUBLICATIONS

The extended European search report issued on Apr. 7, 2015 in the counterpart European patent application.

* cited by examiner

RINSING DEVICE FOR MICROPLATE

CROSS-REFERENCE TO RELATED APPLICATIONS

This application is based upon and claims the benefit of priority from the prior Japanese Patent Application No. 2012-161460 (filed Jul. 20, 2012); the entire contents of which are incorporated herein by reference.

BACKGROUND OF THE INVENTION

Field of the Invention

The present invention relates to a device used in a test using antigen-antibody reactions and in particular relates to a rinsing device for rinsing wells of a microplate used in the test.

Description of the Related Art

Tests of drug discovery screening employ proper containers for liquid samples, such as microplates. In a case of a test using antigen-antibody reactions, prior to observation of reaction results, it is required to rinse surplus samples off the microplate. This rinse is carried out by, for example, expelling a liquid for rinsing onto respective wells of the microplate and next sucking the liquid.

This rinse may utilize a device comprised of both a head for expelling and a head for sucking. Then, in an ordinary procedure, microplate subject to rinsing is moved from under the expelling head to under the sucking head. For the purpose of improving efficiency, some rinsing devices have been proposed, by which microplates are not required to move. Japanese Patent Applications Laid-open No. H07-83939 and No. H07-113728 disclose related arts.

In the prior art frequently used is a 96-well microplate, where diameters of the wells are 7 mm and pitches therebetween are 9 mm. There is in recent years a growing need for using a microplate with a greater number of wells thereon in order to carry out a greater number of test simultaneously. In a 384-well microplate, diameters thereof are 3.6 mm and pitches are 4.5 mm for example. In a 1536-well microplate, diameters thereof are 1.7 mm and pitches are 2.25 mm for example.

SUMMARY OF THE INVENTION

Use of any art disclosed in the aforementioned patent documents in combination with a microplate with a greater number of wells would give rise to difficulties. In a case of a 1536-well microplate, paired nozzles (H07-83939) must be arranged within each 1.7 mm width or double-tubed nozzles (H07-113728) must be arranged every 2.25 mm. In either case, complex and fine structures must be produced with high precision. There must be a high technical hurdle.

The present invention has been achieved in view of the aforementioned problems. According to an aspect of the present invention, a rinsing device is comprised of a rinsing head including a first flow path extending horizontally, and a second flow path extending horizontally and being disposed below or above the first flow path so as not to communicate with the first flow path; one or more nozzles arranged horizontally and projecting vertically downward from the rinsing head; and one or more sliding members including passages in fluid communication with the nozzles, the sliding members slidably fitting in the rinsing head and being movable between a first position to place the passages in fluid communication with the first flow path and a second position to place the passages in fluid communication with the second flow path.

DETAILED DESCRIPTION OF THE PREFERRED EMBODIMENT

Certain embodiments of the present invention will be described hereinafter with reference to the appended drawings. It is noted that the drawings are not scaled and therefore dimensions are not limited to those shown therein.

Figure 1:
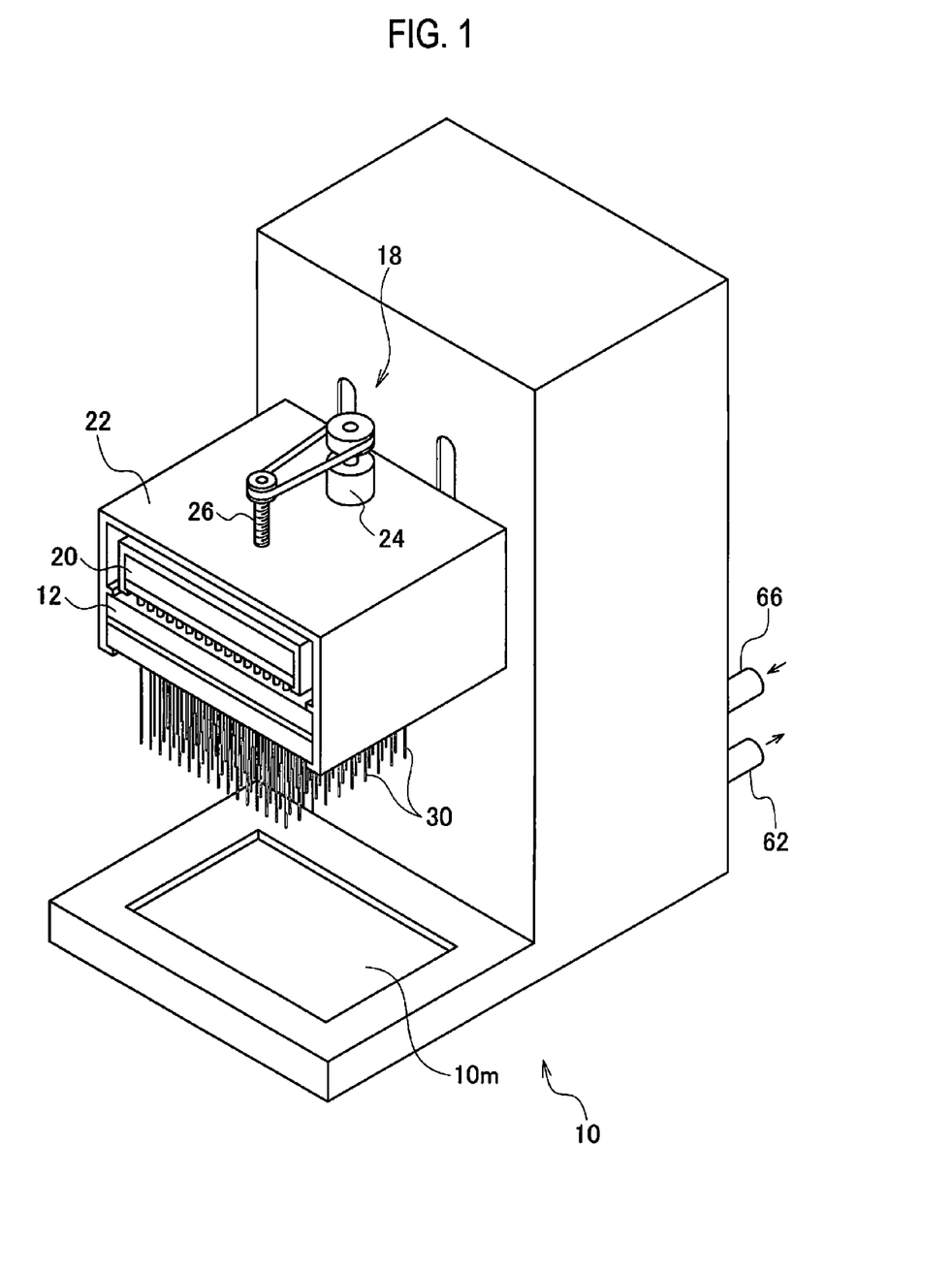
FIG. 1 is a perspective view of a rinsing device of an embodiment of the present invention.

Referring to FIG. 1, a rinsing device 10 of an embodiment of the present invention is applicable to various purposes and is in particular used in rinsing a microplate with multiple wells thereon for biochemical screening tests for example.

Figure 2:
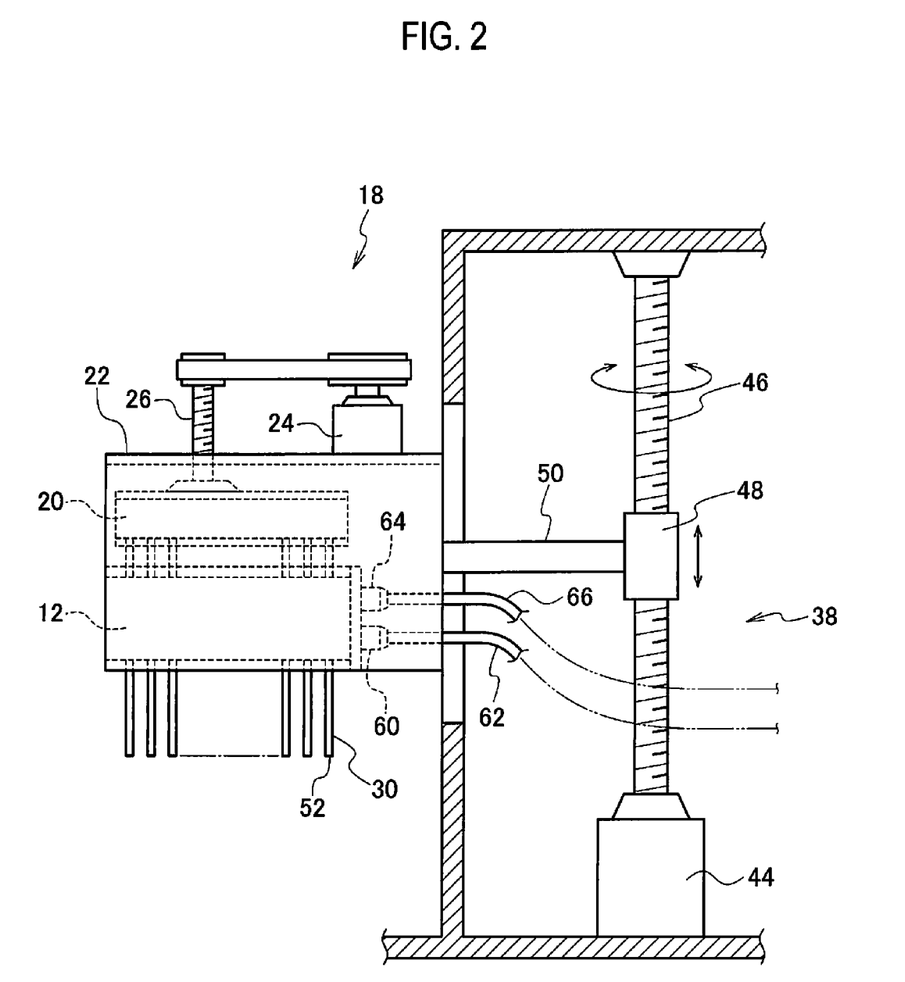
FIG. 2 is a partial cross sectional view of the rinsing device.
Figure 3:
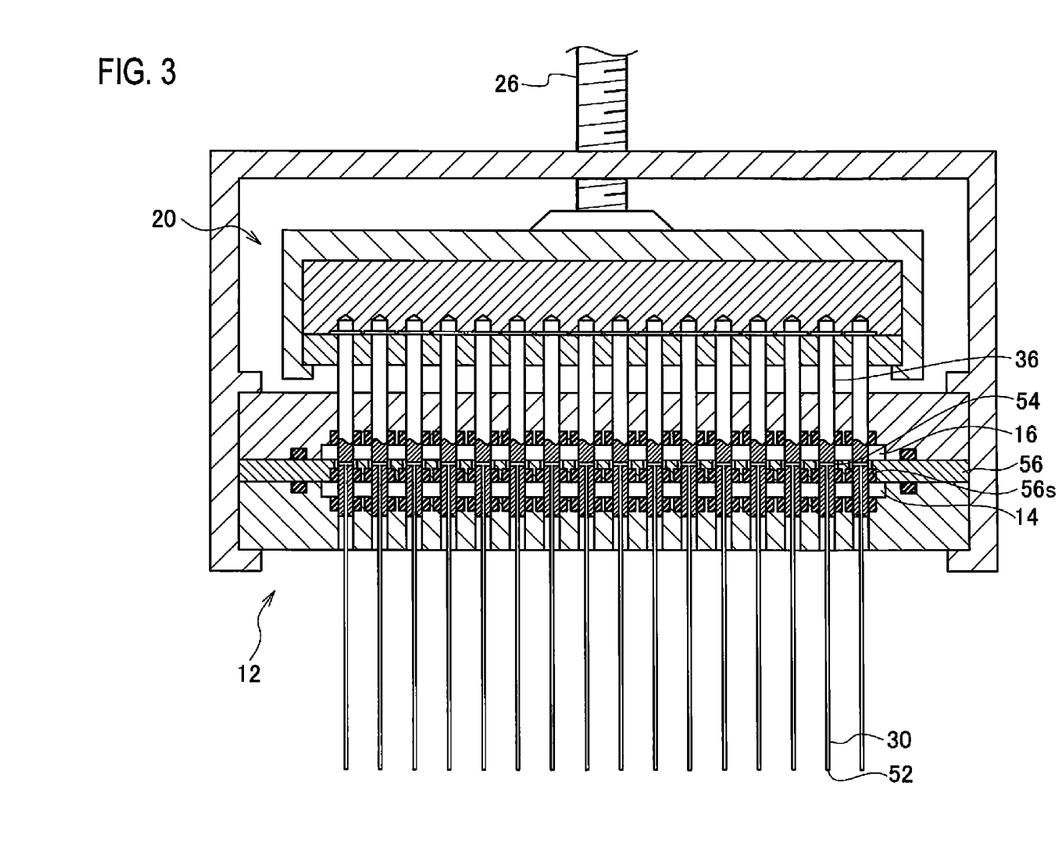
FIG. 3 is an elevational view mainly of a rinsing head of the rinsing device.

Referring to FIGS. 1 through 4C, particularly FIG. 3, the rinsing device 10 is comprised of a rinsing head 12. The rinsing head 12 is comprised of a first flow path 14 extending horizontally, and a second flow path 16 extending horizontally and disposed above (or below) the first flow path 14 so as not to communicate with the first flow path 14. To separate the first flow path 14 from the second flow path 16, an intermediate layer 56 intervenes between the flow paths 14 and 16. It is noted that each flow path 14 or 16 is not limited to a single unitary cavity but may be plural divided cavities arranged in parallel. The first flow path 14 can be used for expelling a rinse fluid into respective wells and the second flow path 16 can be used for sucking the rinse fluid as described later in more detail, whereas this relation may be reversed.

The rinsing device 10 is comprised of a head support 22 for supporting the rinsing head 12. The whole of the rinsing head 12 and the head support 22 is attached to a main body of the device 10 in a vertically movable manner.

Above the rinsing head 12 installed is a support member 20 for supporting a plurality of nozzles. Detailed descriptions about the nozzles will be given later. The support member 20 is, by means of a lifting means 18, made movable up and down relative to the head support 22.

Mainly referring to FIG. 2, the lifting means 18 is also supported by the head support 22. The lifting means 18 is for example comprised of a motor 24 and a ball screw 26. The motor 24 is secured to the head support 22. The ball screw 26 is drivingly coupled with the motor via a belt, a chain, or a gear set. The ball screw 26 penetrates and is threaded in the head support 22, and its lower end is rotatably coupled with the support member 20. Thereby when the motor 24 rotates clockwise or counterclockwise, the support member 20 moves up or down. Alternatively, instead of the combination of the motor 24 and the ball screw 26, any proper driving device such as a hydraulic device, a pneumatic device, or a linear motor may be applied thereto.

Further, the rinsing device 10 is comprised of a plurality of nozzles 30. The nozzles 30 are, as typically shown in FIG. 1, arranged horizontally to form a plurality of rows and a plurality of lines. Alternatively any other proper arrangement or pattern may be possible.

Referring to FIG. 3, each nozzle 30 on its upper part has a sliding member 36 which slidably fits in the rinsing head 12 while its lower part is a thin and elongated nozzle part. The sliding member 36 and the nozzle part may be a single unitary body, or they may be once formed in separate bodies and combined together by means of tight fitting, bonding or such. Each sliding member 36 is so positioned as to penetrate the first flow path 14 and the second flow path 16 and make its nozzle part project downward from the rinsing head 12. The sliding members 36 are elongated upward and secured to the support member 20. Thereby operation of the lifting means 18 causes the nozzles 30 to move up or down.

Figure 4A:
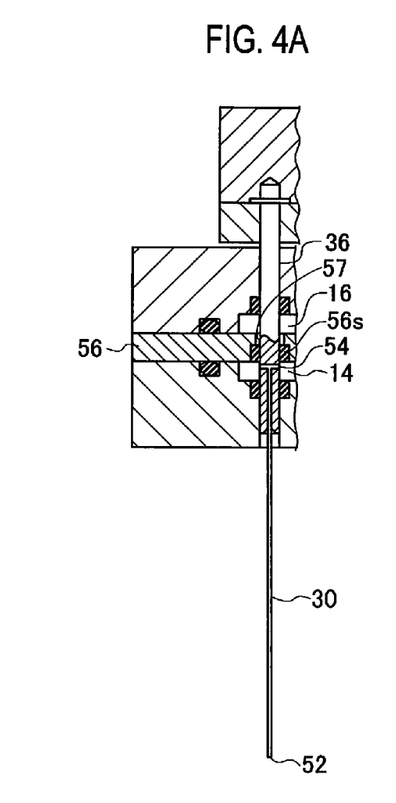
FIG. 4A is an elevational sectional view of the rinsing head in a state where a nozzle is in fluid communication with a flow path for expelling.
Figure 4B:
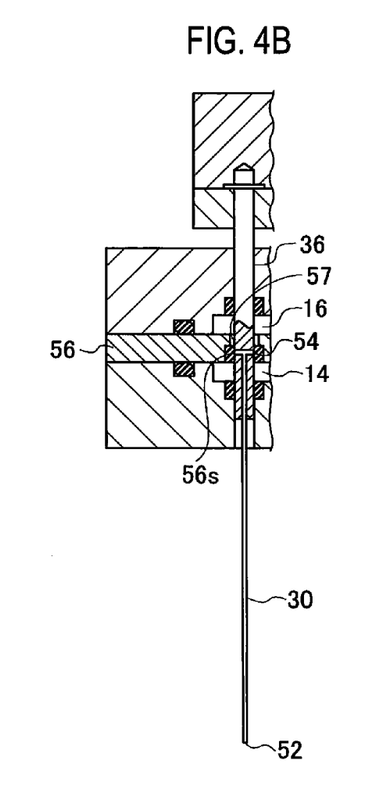
FIG. 4B is an elevational sectional view of the rinsing head in a state where an opening of the nozzle is closed.
Figure 4C:
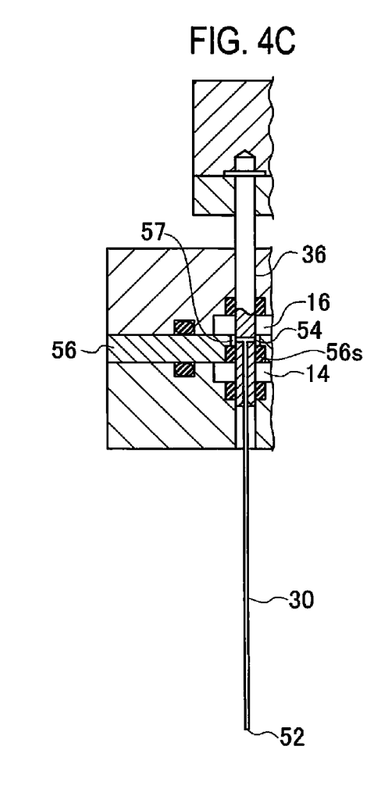
FIG. 4C is an elevational sectional view of the rinsing head in a state where the nozzle is in fluid communication with a flow path for sucking.

Each nozzle 30 is comprised of a passage 52 running throughout the nozzle part to reach the sliding member 36, and an opening 54 in fluid communication with the passage 52. The rinsing liquid can flow through the passage 52 and the opening 54. The opening 54 is for example opened on a side face of the sliding member 36. In turn, the intermediate layer 56 is comprised of blocks 56s positioned correspondingly to the openings 54. The blocks 56s are for example made of any resilient material such as rubber, thereby getting in fluid-tight contact with the openings 54 to close them when aligned together. Referring to FIGS. 4A through 4C, the intermediate layer 56 may have gaps 57 through which the openings 54 are in fluid communication with the second flow path 16 (or the first flow path 14) when the openings 54 come off the respective blocks 56s.

The rinsing device 10 is, within its main body as clearly shown in FIG. 2, comprised of an elevator means 38 for elevating the head support 22. The elevator means 38 is comprised of a motor 44 and a ball screw 46. The motor 44 is for example combined with an end of the ball screw 46, thereby rotating the ball screw 46. In the ball screw 46 threaded is a nut 48 from which an arm 50 is extended and bound to the head support 22. Thereby when the motor 44 rotates clockwise or counterclockwise, the head support 22 moves up or down. Alternatively, instead of the combination of the motor 44 and the ball screw 46, any proper driving device such as a hydraulic device, a pneumatic device, or a linear motor may be applied thereto.

With the first flow path 14 via a connector 60 connected is a first line 62 for pressurizing and injecting a fluid into the first flow path 14. Any pump or pressurizing means is connected to the first line 62, thereby any rinsing liquid or any other fluid is supplied to the first flow path 14 under proper pressure. Similarly the second flow path 16 via a connector 64 connected is a second line 66 for exerting a negative pressure on the second flow path 16. A vacuum pump or any suction means is connected to the second line 66, thereby an exhaust liquid is discharged out of the second flow path 16 under controlled negative pressure. Alternatively the first flow path 14 may be given negative pressure and the second flow path 16 may be given positive pressure instead.

A detent may be provided on or around the connector 60 and correspondingly the first line 62 may have a latching depression. Such a construction is advantageous in readiness of connection and also an operator will readily verify the connection by a clicking sound made when the detent falls into the depression. The same may apply to the combination of the connector 64 and the second line 66.

The rinsing device 10 may be used in a way described below.

Referring to FIG. 1, in an initial state, the head support 22 is properly elevated to bring the nozzles 30 apart from a table 10m of the rinsing device 10 and the head support 22 is, as typically shown in FIG. 4B, properly positioned so that the blocks 56s are respectively aligned to and close the openings 54 of the nozzles 30. Closure by the blocks 56s prevents unintended trickling through the nozzles 30.

An operator places a microplate with multiple wells on the table 10m and then starts the elevator means 38 to move the head support 22 down so that the bottom ends of the nozzles 30 come close to the respective wells of the microplate.

Then the lifting means 18 is driven to move the nozzles 30 down so that the openings 54 depart from the blocks 56s and come in fluid communication with the first flow path 14 as typically shown in FIG. 4A. As the first flow path 14 is filled with the pressurized rinsing liquid, the nozzles 30 expel the rinsing liquid onto the respective wells.

Next the lifting means 18 is driven to move the nozzles 30 up so that the openings 54 go beyond the intermediate layer 56 and come in fluid communication with the second flow path 16 as typically shown in FIG. 4C. As the second flow path 16 is given negative pressure, the liquid on the respective wells are sucked via the nozzles 30.

Alternatively, any modification will occur, in which liquid ejection occurs when the nozzles 30 come up and liquid suction occurs when the nozzles 30 come down for example.

As described above, the rinsing device 10 enables each single nozzle 30 to both expel and suck the rinsing liquid. Neither paired nozzles nor double-tubed nozzles are necessary and therefore complex and fine structures are unnecessary. The present embodiment facilitates use of a microplate with the greater number of wells, such as a 384-well microplate or a 1536-well microplate, although the rinsing device 10 has such a simple structure.

Figure 5A:
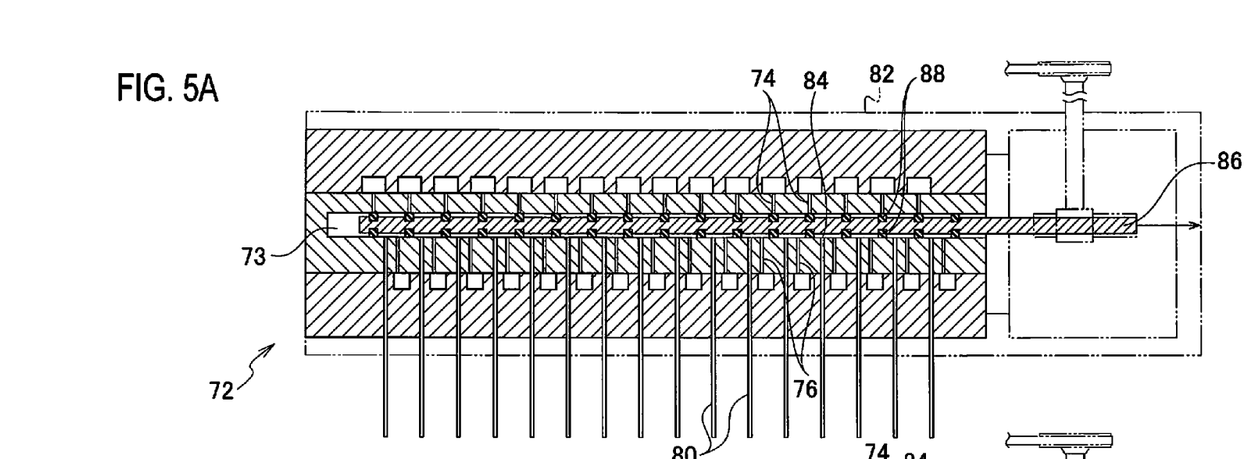
FIG. 5A is an elevational sectional view of a rinsing head according to another embodiment of the present invention in a state where nozzles are in fluid communication with a flow path for expelling.
Figure 5B:
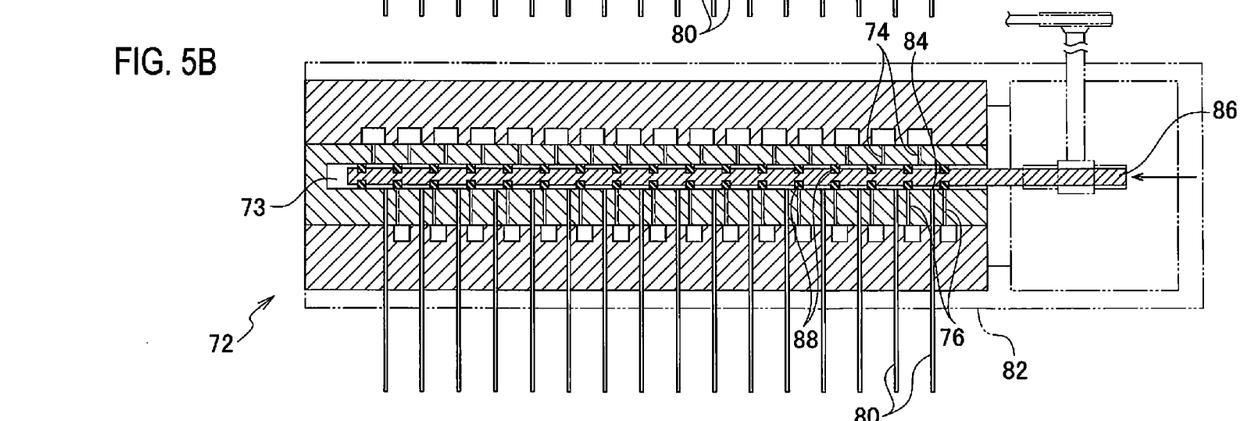
FIG. 5B is an elevational sectional view of the rinsing head in a state where the nozzles are in fluid communication with a flow path for sucking.
Figure 6:
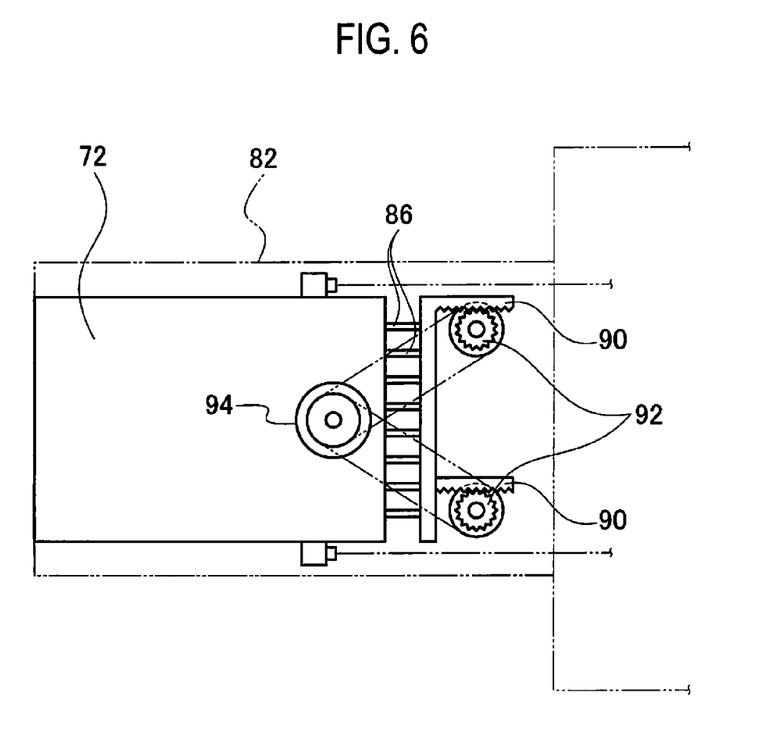
FIG. 6 is a plan view of a device for driving a sliding member for the rinsing head.

Various modifications of the embodiment described above will occur. FIGS. 5A, 5B and 6 exemplify one of such modified embodiments.

Referring to 5A and 5B, a rinsing head 72 is supported by a head support 82. The rinsing head 72 is comprised of a plurality of sliding members 86, while only one of the sliding members 86 appears in these drawings. The sliding members 86 horizontally fit in the rinsing head 72 and are movable in the horizontal direction.

The rinsing head 72 is, as with the case of the aforementioned head support 22, comprised of a first flow path and a second flow path below (or above) the first flow path, both of which are shown as divided cavities in the drawings. From the first flow path extended are first sub-paths 74 and from the second flow path extended are second sub-paths 76.

The rinsing head 72 is comprised of a plurality of nozzles 80 secured thereto and projected downward. The nozzles 80 are arranged horizontally to form a plurality of rows and a plurality of lines. Each nozzle 80 is comprised of a passage therein, which has an opening 84 opened at its upper end.

To close the first sub-paths 74 and the second sub-paths 76, each sliding member 86 is comprised of a plurality of blocks 88 made of any resilient material such as rubber for example. The blocks 88 may be used also for closing the openings 84 of the nozzles 80. At gaps between the sliding members 86 and the passages 84, the sliding member 86 are comprised of passages 73 which allow flow of the rinsing liquid.

When each sliding member 86 is in a first position as typically shown in FIG. 4B, a set of the blocks 88 close the second sub-paths 76 while the openings 83 of the nozzles 80 are in fluid communication with the first sub-paths 74 via the passages 73, thereby expelling the rinsing liquid. When each sliding member 86 is in a second position as typically shown in FIG. 4B, another set of the blocks 88 close the first sub-paths 74 while the openings 83 are in fluid communication with the second sub-paths 76 via the passages 73, thereby sucking the rinsing liquid.

To drive the sliding members 86, the rinsing device is comprised of a driving means as exemplarily shown in FIG. 6. The driving means in general has a so-called rack-and-pinion mechanism comprised of racks 90, pinions 92 respectively meshing with the racks 90, and a motor 94 drivingly coupled with the pinions 92 via belts. When the motor 94 rotates clockwise or counterclockwise, the sliding members 86 move rightward or leftward. Alternatively, any proper driving device such as a hydraulic device, a pneumatic device, or a linear motor may be applied thereto.

The present embodiment serves the same functions and effects as those of the embodiment described above and additionally enables liquid ejection and suction without moving the nozzles 80.

Although the invention has been described above by reference to certain embodiments of the invention, the invention is not limited to the embodiments described above. Modifications and variations of the embodiments described above will occur to those skilled in the art, in light of the above teachings.

What is claimed is:

1. A rinsing device comprising:
   a rinsing head including a first flow path extending horizontally, and a second flow path extending horizontally and being disposed below or above the first flow path so as not to communicate with the first flow path, and an intermediate layer extending horizontally between the first flow path and the second flow path;
   a support member arranged above the rinsing head and controlled by a lifting device for moving up and down;
   a plurality of nozzles attached to the bottom of the support member, and arranged horizontally and projecting vertically downward;
   each nozzle in the plurality of nozzles including a sliding member, a nozzle tip projecting from the sliding member, a passage running throughout the sliding member and the nozzle tip, and an opening located on a side of the sliding member in fluid communication with the passage,
   the sliding members slidably fitting in the rinsing head and being movable between a first position to align the openings with the first flow path to place the passages in fluid communication with the first flow path and a second position to align the openings with the second flow path to place the passages in fluid communication with the second flow path, and
   the intermediate layer comprising a plurality of blocks positioned so that the blocks are in fluidly tight contact with the openings when the openings are positioned in the intermediate layer and are aligned with the blocks.

2. The rinsing device of claim 1, further comprising:
   a first line connected with the first flow path and configured to pressurize and inject a fluid into the first flow path; and
   a second line connected with the second flow path and configured to exert a negative pressure on the second flow path.

3. The rinsing device of claim 1, wherein the sliding members are positioned to penetrate the first flow path and the second flow path and configured to be vertically movable.

* * * * *